US005636287A

United States Patent [19] | [11] Patent Number: 5,636,287
Kubli et al. | [45] Date of Patent: Jun. 3, 1997

[54] APPARATUS AND METHOD FOR THE ACTIVE CONTROL OF AIR MOVING DEVICE NOISE

[75] Inventors: Robert A. Kubli, Milford; Daniel A. Quinlan, Warren, both of N.J.

[73] Assignee: Lucent Technologies Inc., Murray Hill, N.J.

[21] Appl. No.: 346,659

[22] Filed: Nov. 30, 1994

[51] Int. Cl.[6] .......... H03B 29/00; A61F 11/06; H04B 15/00

[52] U.S. Cl. .......... 381/71; 381/94; 415/119

[58] Field of Search .......... 381/71, 94; 248/638; 415/119

[56] References Cited

U.S. PATENT DOCUMENTS

| | | | |
|---|---|---|---|
| 4,817,422 | 4/1989 | Allen | 73/147 |
| 4,837,834 | 6/1989 | Allie | 381/71 |
| 4,947,434 | 8/1990 | Ito | 381/71 |
| 5,010,576 | 4/1991 | Hill | 381/71 |
| 5,117,642 | 6/1992 | Nakanishi et al. | 62/115 |
| 5,127,235 | 7/1992 | Nakanishi et al. | 62/115 |
| 5,386,689 | 2/1995 | Bozich et al. | 381/71 |
| 5,515,444 | 5/1996 | Burdisso et al. | 381/71 |
| 5,548,653 | 8/1996 | Pla et al. | 381/71 |

*Primary Examiner*—Curtis Kuntz
*Assistant Examiner*—Xu Mei

[57] ABSTRACT

Method and apparatus for the active cancellation of broad band noise and/or single frequency tones emanating from rotating machinery, such as an air moving device, by detecting related mechanical and acoustic signals therein and causing canceling vibrations to be applied directly to the rotating machinery by a transducer.

63 Claims, 4 Drawing Sheets

APPARATUS AND METHOD FOR THE ACTIVE CONTROL OF AIR MOVING DEVICE NOISE

BACKGROUND OF THE INVENTION

1. Field of the Invention

This invention relates to the active control and reduction of both tonal and broad band noise in rotating machinery, and in particular to the reduction of tones and noise in air moving devices.

2. Description of Related Art

Rotating equipment emits sounds which are often objectionable to humans or which induce further vibrations in other equipment. The noise is discernible over a broad frequency spectrum, often with significant contributions from the lower end of the frequency spectrum—that below 1000 HZ. Within a broad frequency band of sounds there is a general noise level which may be due to turbulent flow and also high amplitude discrete tones which correspond to the frequency of the repetitive motion of parts of the machinery. The tones are caused by slight imbalances in machine parts, by air moving device blades moving past a stationary object, or by the excitation of natural modes of vibration within each element of the machinery.

Passive control of machine noise includes the use of enclosures which are lined with materials that absorb the offensive acoustic energy. Some machinery, however, requires access for convection cooling of the machinery itself, or openings for the output of the machinery as in the case of air moving devices, compressors, or turbines. Therefore, active methods of control have been devised which sense objectionable sound emanating from rotating machinery, generate additional sound which is out of phase with the detected sound, and thereby lowers or cancels it.

Active control methods typically sense structure-borne vibration or air-borne acoustic noise, or both, operate upon these signal(s), and generate additional sound which is separate from the source of the objectionable noise. For the case of flow induced noise, the radiated noise is related to lift fluctuations caused by the flow. These lift fluctuations can be sensed and used as inputs to a control algorithm.

An example is U.S. Pat. No. 5,117,642 (K. Nakanishi, et. al.) which shows a compressor within a chamber with an opening whose longest lateral dimension is small compared to the wavelength in air of the objectionable noise, a vibration sensor which feeds a control circuit containing a finite impulse response filter, and a sound generator which is mounted close to the opening which delivers acoustic energy into the air. The attempt here is to cancel the offensive sound before it can radiate from the chamber. The same inventors further disclose detecting vibration in a direction tangential to the compressor in U.S. Pat. No. 5,127,235.

U.S. Pat. 5,010,576 (P. D. Hill) teaches the use of an accelerometer which detects imbalances on a multiblade air moving device, a speaker which is mounted facing the air moving device and coaxial with its hub, a microphone which detects the sounds from both the air moving device and the speaker, and the use of a least mean square adaptive filter which accommodates for a time differential in the sounds reaching the microphone. Cancellation of the objectionable sound is made by generation of an out-of-phase acoustic signal generated by a nearby loudspeaker.

U.S. Pat. No. 4,837,834 (M. C. Allie) discloses the acoustic attenuation of noise in ducts whereby one microphone senses noise at an upstream point in the duct, a speaker introduces canceling sound into a mid portion of the duct, and another error sensing microphone senses the resultant acoustic field at a downstream position. The invention is primarily directed to signal filtering, processing, and modeling to drive loudspeakers which cancel sounds in the air.

U.S. Pat. No. 4,817,422 (R. M. Allen) shows an aeroacoustic wind tunnel test apparatus wherein one or more acoustic coupling means inject sound into the upstream end of a flow passage at predetermined intervals. A loudspeaker driver transmits sound along the longitudinal axis of the apparatus.

In the electronic arts there is an ongoing exponential increase in the number of electronic components per unit volume of space. This trend accentuates the need to remove heat which is generated by each component. Air moving devices which provide forced air cooling within component enclosures are also required to decrease in size or else the ratio of packaging volume to active component volume becomes unacceptably large. Less space is also available for passive sound filters and absorbers. Similarly, small cooling air moving devices running at high speeds are used resulting in high tonal and broad band noise levels.

Accordingly, there is an increased need for active intervention to detect and cancel both tones and broad band noise on rotating machinery, and particularly in air moving devices for cooling electronic equipment.

SUMMARY OF THE INVENTION

The present invention relates to apparatus and a method to actively control, and thereby reduce, both discrete frequency tones and broad band noise emanating from air moving devices such as an axial fan, centrifugal blower, mixed flow fan, compressor, propeller, or the blades of a driven turbine. More particularly, the invention concerns the generation of cancellation signals by the rotating equipment itself.

In one embodiment of the invention, an error sensor detects sounds which are objectionable in the operation of rotating machinery. This can be a pressure sensing device such as a microphone which is separate and mechanically disengaged from the rotating machinery. An error signal is thereby generated which is directed into a control circuit. Apparatus for sensing motion generates a separate motion signal which is also directed into the control circuit. The latter may include a common tachometer, or circuitry which receives an optical input of motor motion or of impeller motion.

A control circuit processes the error signal and motion signal in any manner known to the art including, but not limited to: filtering, analog to digital conversion (and the reverse), signal processing, comparison or operation of an algorithm or program, amplification, delay, or any form of analog control.

The output of the control circuit is an actuator signal directed to an actuator via a slip ring. Importantly, the actuator is mounted directly upon the rotating machinery, being attached on one side to a driving shaft and on the other side to rotating machinery which is slideably connected to the driving shaft to receive a torque about its axis. The actuator causes the rotating machinery to move along its axis according to the actuator signal to impart at least one frequency of vibration (or a specific frequency spectrum of vibrations) directly into the rotating machinery to cancel or minimize noise emitted by the machinery. The actuator may be a piezoelectric transducer, an electromagnetic transducer, or an electrostatic device. The driven component therefore becomes the acoustic radiator of the correction signal.

In another embodiment of the invention, a control circuit, an error sensor, a vibration sensor, and an actuator are all mounted upon the driven portion of the rotating machinery, typically in a hub which may be part of an air moving device. The vibration sensor detects acoustic or mechanical vibrations, or both, from the machinery. The error sensor supplies a signal which is to be minimized. Both signals are directed to a control circuit which drives an actuator connected to the rotating machinery to move it along its axis of rotation to minimize noise which is comprised of at least one discrete frequency or a spectrum of frequencies.

In a further embodiment of the invention, a means for sensing force, such as an accelerometer or a piezoelectric strain gauge is mounted directly to the rotating machinery to directly receive fluid dynamically induced machinery vibrations. This force signal is then directed to the aforementioned control circuit.

The control circuit processes the force signal in any manner known to the art including, but not limited to: filtering, analog to digital conversion (and the reverse), signal processing, comparison or operation of an algorithm or program, amplification, delay, or any form of analog control.

In yet another embodiment of the invention, the output of the control circuit is fed to a group of piezoelectric elements mounted directly upon impeller blades of the rotating machinery. The piezoelectric elements radiate directly, or cause the blade to radiate at least one frequency, thereby canceling tones emanating from the machinery. If required, such an arrangement can be used to vary the acoustic directivity of the driven impeller.

The present invention also relates to a method for controlling objectionable tones and broad band noise generated by rotating machinery by sensing an error tone emanating therefrom; generating a motion signal; filtering frequency components of said signals; converting filtered analog signals to digital form; comparing digital signals with an algorithm; generating a corresponding actuator signal; converting the actuator signal from digital to analog form; and driving an actuator whereby forces are imparted upon the rotating machinery to cancel noise generated therein.

An advantage of the present invention is the avoidance of an acoustic speaker, separate and apart from the rotating machinery, to cancel machine noise. This is particularly effective at low frequencies where the separation distance between noise source and control source limits cancellation performance.

Another advantage is that a transducer, in the form of a mechanical actuator or an oscillating piezoelectric element, is mounted directly upon the rotating machinery, thereby reducing performance and stability problems associated with the prior art.

These and other features and advantages of the invention will be better understood with consideration of the following detailed description of the preferred embodiments taken in conjunction with the accompanying drawings.

DETAILED DESCRIPTION OF THE PREFERRED EMBODIMENTS

Figure 1A:
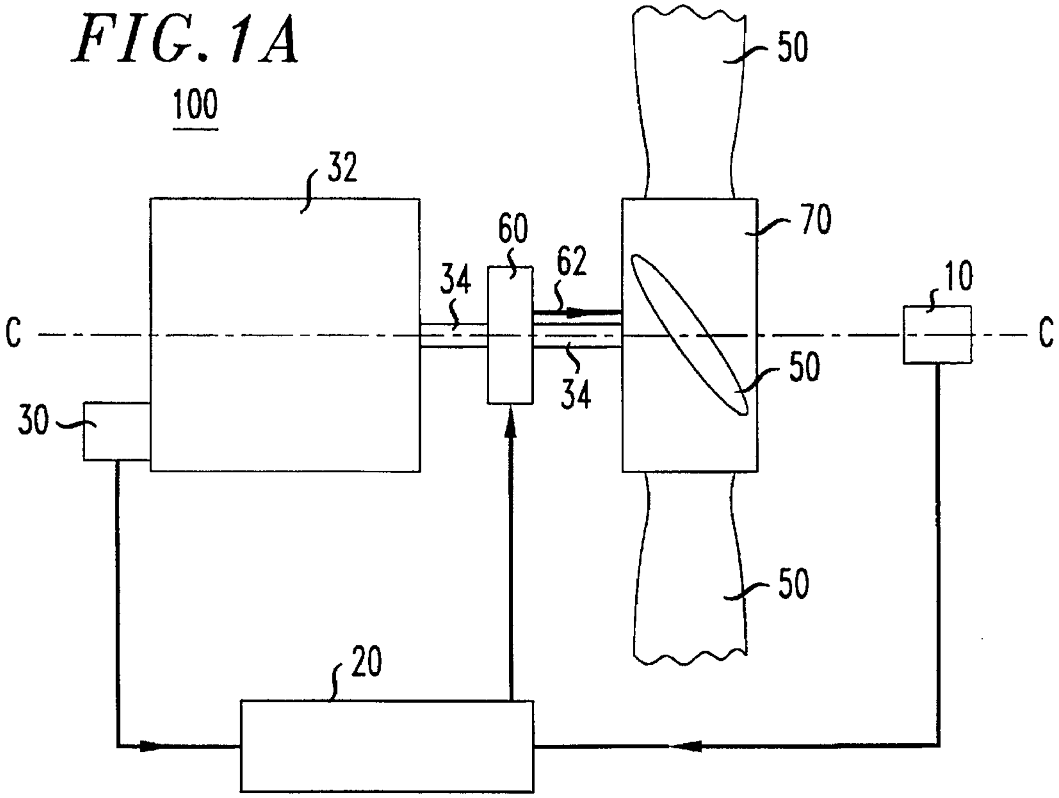
FIG. 1A shows a block diagram depicting apparatus in accordance with one embodiment of the invention whereby noise generated by rotating machinery is reduced by canceling sound generated by the rotating machinery.

Referring now to FIG. 1A, there is shown apparatus 100 in accordance with one embodiment of the invention. An error sensor 10 detects objectionable noise emanating from rotating machinery. This noise has a broad spectrum of frequencies within which are some prominent discrete frequency tones, together with their harmonic multiples. These tones arise from unsteady lift fluctuations, and from periodic events in the motion of the machinery. In practice, the most objectionable discrete tones occur below 1000 Hertz.

Error sensor 10 may be an acoustic pressure sensing device or a common microphone which converts noise below 20 KHz to an electronic error signal which is fed into control circuit 20. Error sensor 10 may also consist of an array of microphones. A means for sensing motion 30 detects periodic events in motor 32. This means may include a tachometer which senses motor speed, or an optical sensor which detects the passage of any portion of the machinery, say motor poles or impeller blades. An electric motion signal is fed from sensing means 30 to control circuit 20.

The control circuit processes the aforementioned signals in a manner well known in the art which includes the operations of: frequency filtering, amplitude detection, analog to digital conversion, signal processing, the use of an algorithm or program, digital to analog conversion, amplification, delay, or any form of analog control. The output of the control circuit is an actuator signal which is directed to slip ring 60 so that the actuator signal is conducted by signal lead 62 along motor shaft 34 into hub 70. A multiplicity of blades 50 are mounted upon hub 70 to form an impeller which is connected to motor shaft 34 by a spline, so that the hub and blade assembly may be driven back and forth along center-line C—C in accordance with the actuator signal from the control circuit. Blades 50 may be components of an air moving device such as an axial fan, centrifugal blower, mixed flow fan, compressor, propeller, or a turbine.

Figure 1B:
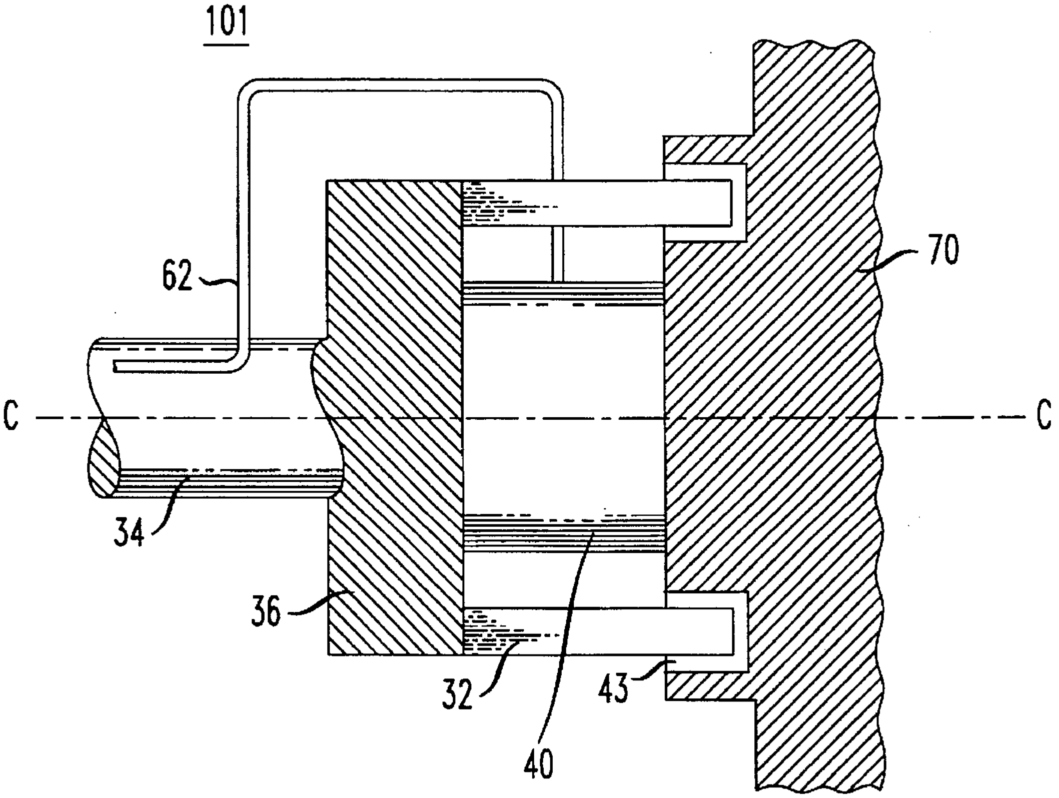
FIG. 1B shows a sectional view of part of the apparatus of FIG. 1A.

Referring now to FIG. 1B, there is shown apparatus 101, which is a partial cross section of the elements within hub 70. Signal lead 62 delivers the actuator signal to actuator 40 which converts the electrical signal into mechanical motion in any manner known in the art including piezoelectric conversion by a piezoelectric material, electromagnetic conversion, or electrostatic conversion. The actuator is mounted between and attached to driving hub 36, which is attached to shaft 34, and hub 70 which is also driven in a circular motion by tines 38 which emanate from driving hub 36. Tines 38 cooperate with one or more splines 43 machined into hub 70 so that it may be driven in a circular motion about axis C—C by motor 32. The actuator drives the hub along axis C—C in accordance with a noise reduction algorithm operating the control circuit to reduce the acoustic pressure at sensor 10.

An extended shaft may be used to couple the actuator to blades 50. In this case the reduced cross-sectional area of the shaft as compared to a conventional hub results in greater through flow area for a given diameter.

Figure 2A:
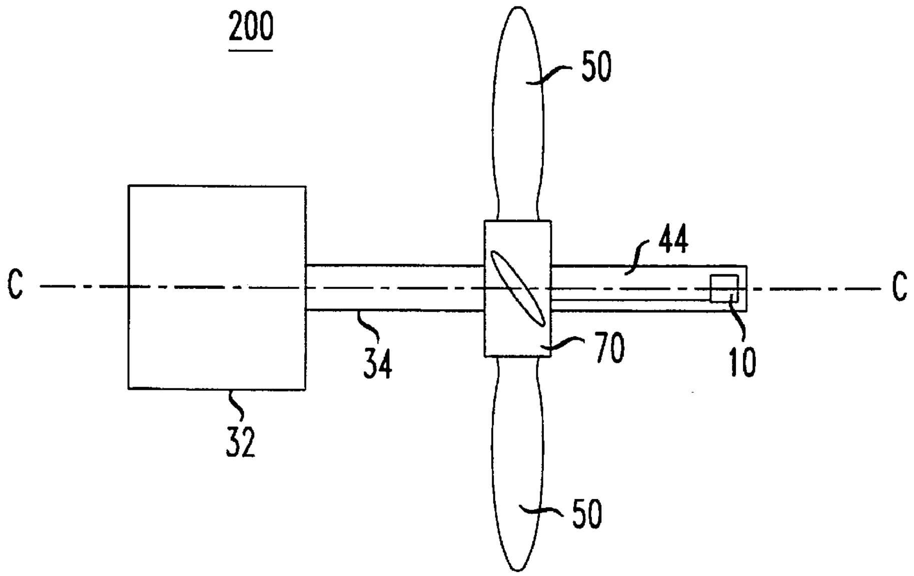
FIG. 2A is a block diagram of apparatus in accordance another embodiment of the invention.

Referring now to FIG. 2A, there is shown apparatus 200 in accordance with another embodiment of the same invention. Motor 32 drives motor shaft 34 which is connected to hub 70 which supports one or more blades 50 to form an impeller, which may be that of an air moving device such as an axial fan, centrifugal blower, mixed flow fan, compressor, propeller, or turbine. An error sensor 10 converts acoustic pressure variations into an electrical signal which is transmitted into the hub via error signal lead 11. Error sensor 10 may be mounted directly to the rotating hub 70 or to extension 44 to the hub. Error sensor 10 is a device which detects acoustic pressure variations below 20 KHz and may be an ordinary microphone.

Figure 2B:
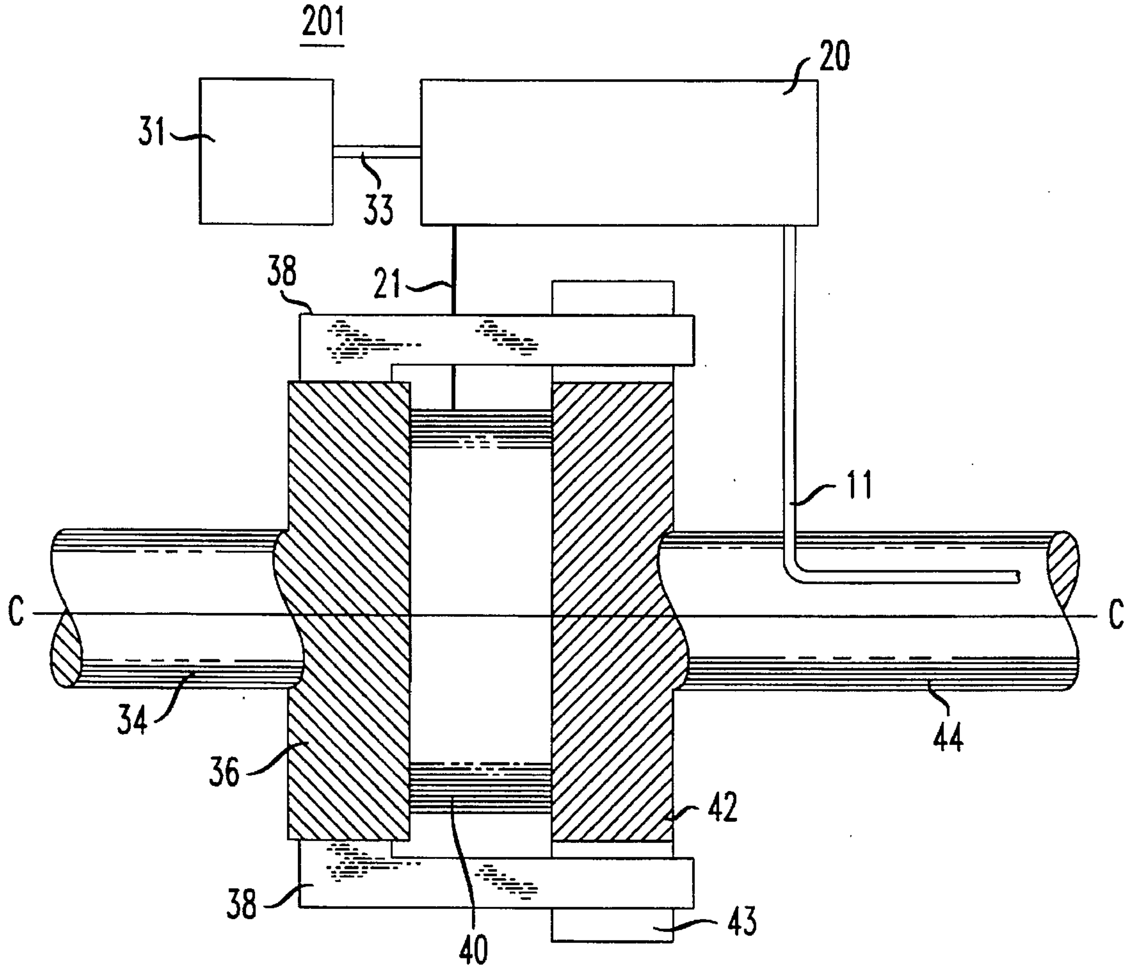
FIG. 2B and FIG. 2C show sectional views of various apparatus in FIG. 2A.

Referring now to FIG. 2B, there is shown apparatus 201 comprising elements of this embodiment which are mounted within the hub. Error signal lead 11 is directed into control circuit 20. Vibration sensor 31 detects acoustic vibrations, mechanical vibrations, or both, which emanate from the motor and blades. An electrical signal generated by the vibration sensor is transmitted via vibration signal lead 33 into the control circuit. The control circuit processes the aforementioned signals in a manner well known in the art which includes the operations of: frequency filtering, amplitude detection, analog to digital conversion, signal processing, the use of an algorithm or program, digital to analog conversion, amplification, delay, or any form of analog control.

Actuator 40 rotates with motor shaft 34 and is mounted to it or to an intermediate motor hub 36. The actuator is also mounted to hub 70 or an extension 44 thereof. Actuator 40 may be a piezoelectric device, an electromagnetic device, or an electrostatic device which converts the actuator signal into mechanical motion which is directed along axis C—C to move the hub itself or its extension. The hub is also driven about axis C—C by a spline connected to motor shaft 34, one possible arrangement of which is the cooperation of tine 38 and spline 43 which is defined by extension 44 or by actuator hub 42 which is interspersed between the actuator and extension 44. The mechanical details of transmitting a torque from a fixed source to a slideably connected driven member are well known. Also, electric power to the elements within the hub is supplied by a slip ring (not shown) which is well known in the art, or could be supplied via a battery located within the rotating apparatus.

Figure 2C:
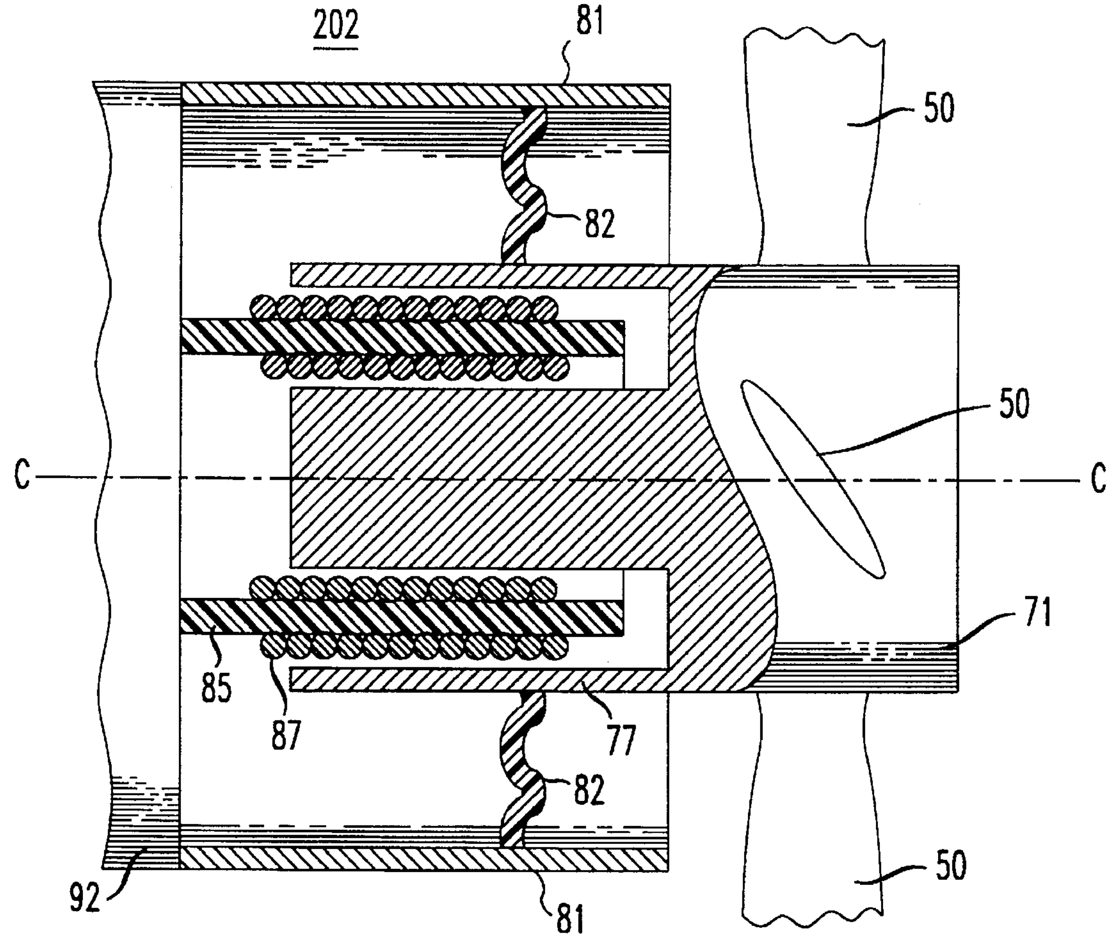

Referring now to FIG. 2C, there is shown apparatus 202 according to another embodiment wherein an electromagnetic actuator imparts a motion to hub 71 along the axis of rotation C—C. Elements with the same function as the preceding figures have the same reference numbers. Support 81 and coil support 85 are mounted to rotary mount 92 which is driven by a motor (not shown) about axis C—C. Flexible coupling 82 is mounted on one end to support 81 and on the other end to hub 71, thereby transmitting a torque from the motor to the hub. Coils 87 are supported by coil supports 85 which rotate with the rotary mount. An actuator signal flowing in coils 87 from a control circuit (not shown) creates a magnetic field around the coils which interacts with pole piece—magnet assembly 77, mounted to the hub, to cause the hub to move along axis C—C. The principle of operation being the same as that of a loudspeaker. A similar mechanical configuration employing a rotating coil and fixed pole-piece magnet assembly would achieve the same result. A similar mechanical configuration employing coupling 82 would support an electrostatic or piezoelectric actuator.

The operation of apparatus 200 to control noise is the same as apparatus 100.

Figure 3:
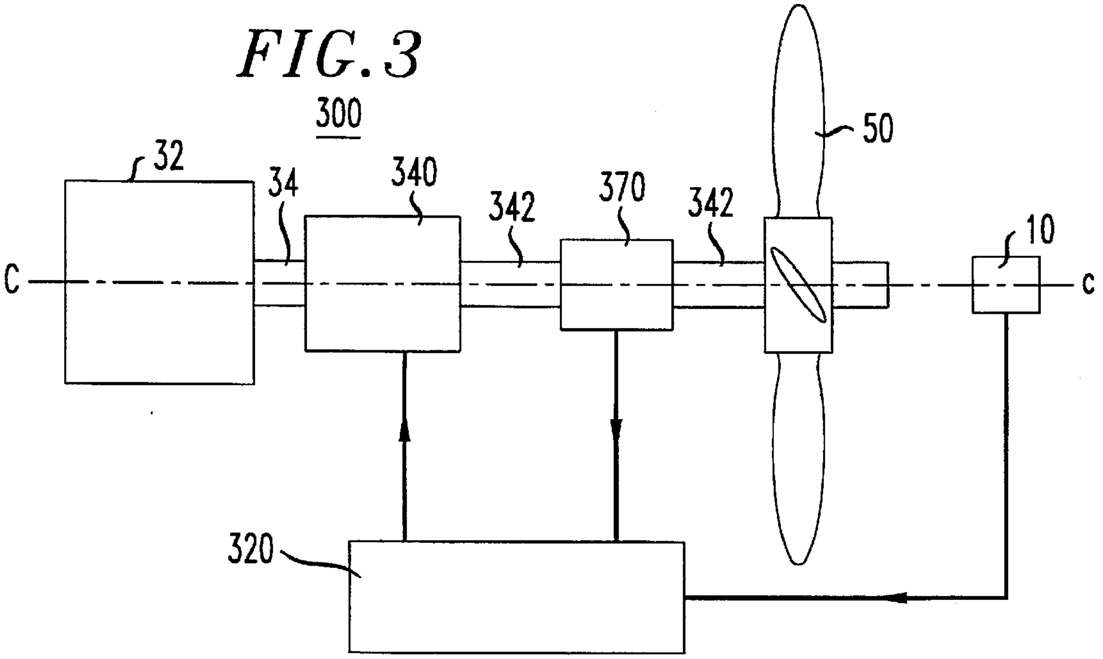
FIG. 3 and FIG. 4 show block diagrams in accordance with other embodiments of the invention.

Referring now to FIG. 3, there is shown apparatus 300 which reduces broad band noise in accordance with another embodiment of the invention. Where the elements of apparatus 300 are the same as apparatus 100 the same reference numbers are shown.

In apparatus 300, one or more blades 50 are mounted upon actuator shaft 342 which is rotated by motor shaft 34. The connection between shaft 342 and motor shaft 34 is a spline or equivalent. Actuator shaft 342 is also driven in a direction along its major axis by actuator 340 which receives an actuator signal from control circuit 320. The input to control circuit 320 is a signal from a means for sensing force 370 which senses vibrations in actuator shaft 342. Force sensing means 370 may be a piezoelectric material, an electrostatic sensor, or an electromagnetic sensor, or an accelerometer which is attached to actuator shaft 342 whereby a machine force signal is fed to the control circuit by a slip ring, (not shown). Force sensing means 370 may also be an optical sensor which is fixed near actuator shaft 342 whereby vibrations in the shaft are detected and a machine force signal in either optical or electronic form is sent to control circuit 320. Force sensing means 370 may also be mounted on motor shaft 34 or on motor 32.

Control circuit 320 processes the machine force signal by operations, well known in the art, which include: frequency filtering, amplitude detection, analog to digital conversion, signal processing, the use of an algorithm or program, digital to analog conversion, amplification, or delay. As with previously described embodiments, the control circuit 320 can be internal to the actuator housing or may be externally connected via a slip ring or telemetry.

The output from control circuit 320 is a broad band signal, which can include some high amplitude discrete frequency tones, which cause actuator 340 to move actuator shaft 342 whereby broad band noise emanating from rotating machinery is reduced.

An error sensor 10, previously described in FIG. 1, is employed to provide an input error noise signal to control circuit 320. As with previously described embodiments, the error sensor(s) 10 can be integral to the rotating apparatus or may be externally connected via a slip ring or telemetry. The algorithm or program operating the control circuit processes both the error noise signal and the machine force signal to reduce broad band noise emanating from apparatus 300.

Figure 4:
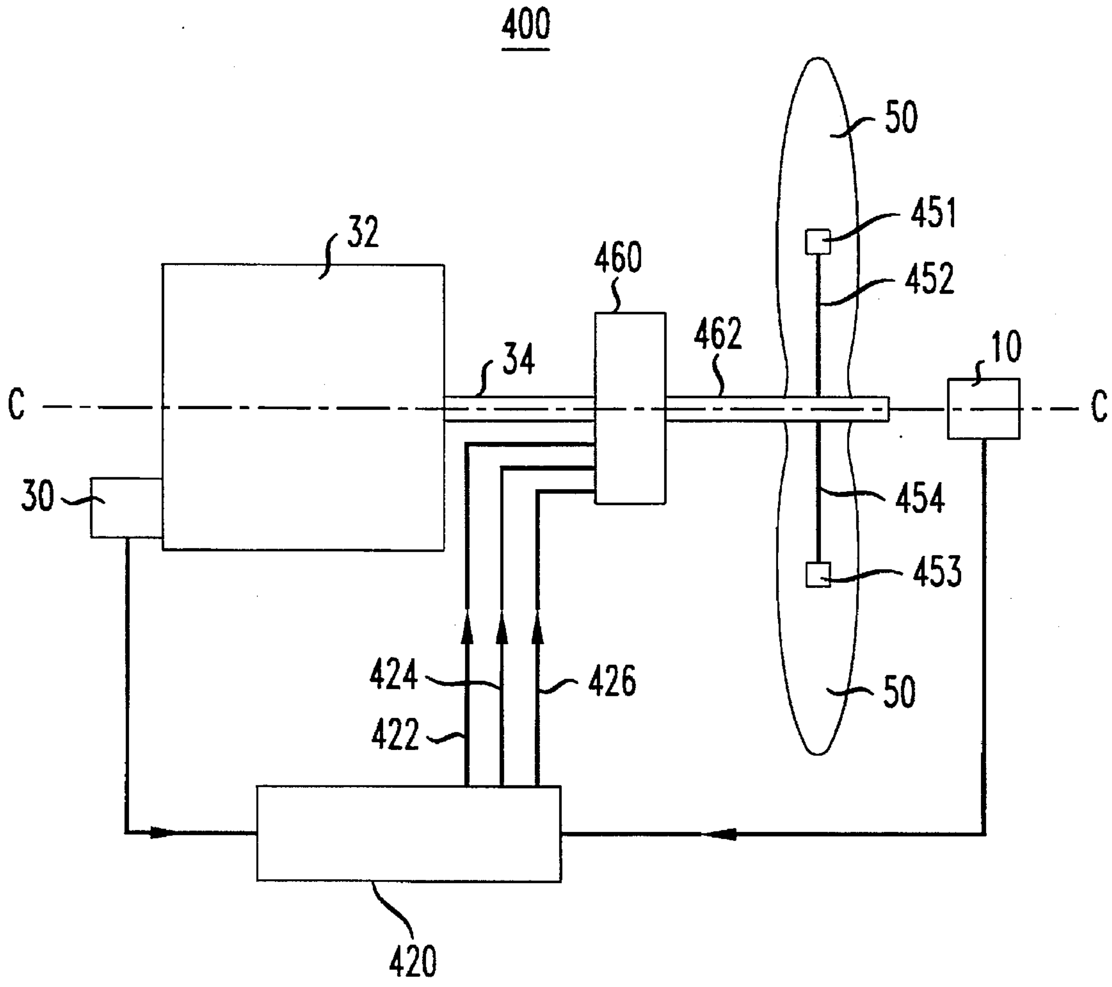

Referring now to FIG. 4, there is shown apparatus 400 in accordance with yet another embodiment of the invention.

In apparatus 400, motor 32 drives motor shaft 34 upon which are mounted one or more blades 50. Mounted upon each blade 50 are piezoelectric elements 451, 453, etc. These elements could also be mounted to the impeller hub. Conductors 452, 454, etc. electrically connect piezoelectric elements 451, 453, etc. to slip ring 460 by passing along or within each blade and along or within shaft 34. The operation of a slip ring to communicate signals is very well known in the art.

The operation of means for sensing motion 30 and error sensor 10 are the same as described in FIG. 1 or FIG. 3, and are incorporated here. For the case where control circuit 420 has been miniaturized, the number of signals passed through a slip ring or telemetry system can be reduced depending upon the configuration.

Control circuit 420 receives signals from the means for sensing motion and the error sensor and processes these signals in a manner well known in the art which includes the operations of: analog control, frequency filtering, amplitude detection, analog to digital conversion, signal processing, the use of an algorithm or program, digital to analog conversion, amplification, delay, or any form of analog control. The output of the control circuit is at least one piezoelectric element signal which signal(s) are delivered to slip ring 460 along conductors 422, 424, 426, etc. and are directed to conductors 452, 454, etc. to each separate piezoelectric element 451, 453, etc., where one piezoelectric element is mounted to each blade 50 and/or the impeller hub. Piezoelectric element(s) 451, 453, etc. are typically transducers made from a piezoelectric material which transform electrical energy to mechanical motion. Their operation is well known in the art.

In operation each piezoelectric element signal may be equal in phase and in amplitude, each piezoelectric element signal may differ in phase from all the other piezoelectric element signals, each piezoelectric element signal may differ in amplitude from all the other piezoelectric element signals, or each piezoelectric element signal may differ in frequency from all the other piezoelectric element signals. Indeed each piezoelectric element signal may be entirely different from every other one. The result is that each piezoelectric element radiates acoustic energy, or each blade acts as an acoustic baffle for its piezoelectric element. In either case, an acoustic signal is generated to directly cancel or reduce noise which otherwise emanates from the rotating machinery.

The advantage over the use of a separate acoustic speaker to generate canceling sound waves is that the volume of the speaker is eliminated, particularly for low frequencies, and the limitations of a dipole canceling scheme where two sound sources are separated by a distance are eliminated. It is well known in active control of sound, that as the physical dimensions of the original noise source and its associated canceling source(s) become large with respect to wavelength, the ability to reduce radiated sound decreases. In this invention, objectionable noise generated by rotating machinery is directly canceled by vibrations induced into the machinery itself.

Tones generated by rotating machinery may be controlled by sensing an objectionable error signal emanating therefrom. This is typically done by sensing machinery motion to generate a motion signal, filtering frequency components of said signal, converting filtered analog signals to digital form, comparing digital signals with an algorithm, generating an actuator signal, converting the actuator signal from digital to analog form, and driving an actuator whereby forces are impressed upon the rotating machinery to cancel tones generated therein.

Broad band noise generated by rotating machinery may be controlled by sensing forces caused by the rotating machinery to generate a machine force signal, sensing error noise to generate an error noise signal, converting said signals to digital form, comparing said digital signals, applying an algorithm or program to said digital signals, generating an actuator signal, converting the actuator signal to analog form, and driving an actuator mounted on the air moving device whereby forces are impressed directly upon the air moving device to control broad band noise which may include some predominant single frequency tones.

Noise generated by rotating machinery may also be reduced by sensing machinery motion to generate a motion signal, processing the aforementioned signals to generate a group of piezoelectric element signals, and directing a separate piezoelectric element signal to a piezoelectric element mounted on rotating surfaces of the machinery to induce vibrations in the piezoelectric element, whereby noise caused by the rotating surfaces and their drive motor are reduced.

Changes and modifications in the specifically described embodiments can be carried out without departing from the scope of the invention. In particular, the apparatus and method described for controlling tones and noise in the various embodiments may be combined in one apparatus and operation. The error sensor may be an array of microphones which need not be located upon a centerline through the apparatus.

We claim:

1. Apparatus for the control of noise generated by rotating machinery comprising:

at least one error sensor;

means for sensing motion;

a control circuit for receiving signals from the error sensor and the motion sensing means, which control circuit develops an actuator signal;

an actuator attached to a motor shaft, which receives the actuator signal from the control circuit and transforms it into mechanical motion causing rotating machinery attached to the actuator to move along an axis; and a slip ring which receives the actuator signal from the control circuit and which connects said signal to the actuator.

2. Apparatus of claim 1 wherein the error sensor includes at least one microphone.

3. Apparatus of claim 1 wherein the motion sensor means includes a tachometer.

4. Apparatus of claim 1 wherein the motion sensor means is optically coupled to the rotating machinery.

5. Apparatus of claim 1 wherein the control circuit includes filters, analog to digital converters, signal processors, digital to analog converters, and amplifiers which generate an actuator signal.

6. Apparatus of claim 1 wherein the actuator drives a hub along its longitudinal axis in accordance with the actuator signal from the control circuit, whereby at least one frequency of vibration is generated which cancels one or more tones generated by the rotating machinery.

7. Apparatus of claim 1 wherein the actuator is a piezoelectric material.

8. Apparatus for the control of noise generated by an air moving device comprising:

at least one microphone;

a tachometer;

a control circuit for receiving signals from the microphone and the tachometer, which control circuit develops an actuator signal;

a piezoelectric actuator attached to a motor shaft, which receives the actuator signal from the control circuit and transforms it into mechanical motion causing an impeller attached to the piezoelectric actuator to move along an axis; and a slip ring which receives the actuator signal from the control circuit and which connects said signal to the piezoelectric actuator.

9. Apparatus for the control of noise generated by rotating machinery comprising:

a hub, slideably connected to a motor, being rotatable about an axis;

an error sensor mounted to the hub;

a vibration sensor mounted to the hub;

a control circuit, mounted to the hub, which receives signals from the error sensor and the vibration sensor, which control circuit develops at least one actuator signal; and an actuator attached to a motor, which receives the actuator signal from the control circuit and transforms it into mechanical motion causing the hub to move along its axis.

10. Apparatus of claim 9 wherein the error sensor includes a microphone.

11. Apparatus of claim 9 wherein the vibration sensor detects acoustic vibrations.

12. Apparatus of claim 9 wherein the vibration sensor detects mechanical vibrations in the rotating machinery.

13. Apparatus of claim 9 wherein the control circuit includes filters, analog to digital converters, signal processors, digital to analog converters, and amplifiers which generate an actuator signal.

14. Apparatus of claim 9 wherein the hub supports at least one blade.

15. Apparatus of claim 9 wherein the actuator is a piezoelectric material.

16. Apparatus of claim 9 wherein the actuator is an electromagnetic transducer.

17. Apparatus of claim 9 wherein the actuator is an electrostatic transducer.

18. Apparatus for the control of noise generated by an air moving device comprising:

a hub, supporting at least one blade, slideably connected to a motor, being rotatable about an axis;

a microphone mounted to the hub;

a vibration sensor mounted to the hub;

a control circuit mounted to the hub, which receives signals from the microphone and the vibration sensor, which control circuit develops at least one actuator signal; and an actuator attached to a motor, which receives the actuator signal from the control circuit and transforms it into mechanical motion causing the hub to move along its axis thereby, canceling one or more tones generated by the air moving device.

19. Apparatus for the control of noise generated by rotating machinery comprising:

means for sensing force mounted directly upon the rotating machinery;

a control circuit receiving a signal from the force sensing means, which develops an actuator signal;

an actuator shaft driven in a circular motion by a motor, which actuator shaft supports one or more blades; and, an actuator attached to the actuator shaft which receives the actuator signal from the control circuit whereby the actuator shaft is driven in a broad band of frequencies along its axis.

20. Apparatus of claim 19 further comprising an error sensor mounted independently from the rotating machinery, which error sensor sends an error signal to the control circuit.

21. Apparatus of claim 20 wherein the error sensor includes at least one microphone.

22. Apparatus of claim 19 wherein the means for sensing force is mounted on the actuator shaft.

23. Apparatus of claim 19 wherein the means for sensing force is mounted on a shaft between the motor and the actuator.

24. Apparatus of claim 19 wherein the means for sensing force includes an accelerometer.

25. Apparatus of claim 19 wherein the means for sensing force is optically coupled to the rotating machinery.

26. Apparatus of claim 19 wherein the actuator drives the actuator shaft along its longitudinal axis in accordance with the actuator signal from the control circuit whereby discrete frequency tones are generated which cancel noise from the rotating machinery.

27. Apparatus for the control of noise generated by an air moving device comprising:

at least one microphone;

an accelerometer mounted on a motor;

a control circuit receiving signals from the microphone and the accelerometer, which develops an actuator signal;

an actuator shaft driven in a circular motion by a motor, which actuator shaft supports one or more blades; and, an actuator attached to the actuator shaft which receives the actuator signal from the control circuit whereby the actuator shaft is driven in a spectrum of frequencies which cancel noise from the rotating air moving device.

28. Apparatus for the control of noise generated by rotating machinery comprising:

at least one error sensor;

means for sensing motion;

a control circuit for receiving signals from the error sensor and the motion sensing means, which control circuit develops at least one piezoelectric element signal;

a motor shaft driven in a circular motion by a motor, which motor shaft supports at least one blade;

at least one piezoelectric element mounted to each blade; and a slip ring which receives at least one piezoelectric element signal from the control circuit and which connects at least one piezoelectric element signal to at least one piezoelectric element.

29. The apparatus of claim 28 wherein the piezoelectric element is mounted to a hub.

30. Apparatus of claim 28 wherein the error sensor includes at least one microphone.

31. Apparatus of claim 28 wherein the motion sensor means includes a tachometer.

32. Apparatus of claim 28 wherein the motion sensor means is optically coupled to the rotating machinery.

33. Apparatus of claim 28 wherein the control circuit includes filters, analog to digital converters, signal processors, digital to analog converters, and amplifiers which generate an piezoelectric element signal.

34. Apparatus of claim 28 wherein the piezoelectric element includes a piezoelectric transducer which is driven by the control circuit.

35. Apparatus of claim 28 wherein each piezoelectric element receives the same signal from the control circuit.

36. Apparatus of claim 28 wherein each piezoelectric element receives a signal which is different in phase from signals directed to other piezoelectric elements.

37. Apparatus of claim 28 wherein one said piezoelectric element receives a signal which is different in amplitude from signals directed to any other said piezoelectric signal.

38. Apparatus of claim 28 wherein each piezoelectric element receives a signal which is different in frequency from signals directed to other piezoelectric elements.

39. Apparatus for the control of noise generated by an air moving device comprising:

at least one microphone for sensing tones;

a tachometer for sensing motion of the air moving device;

a control circuit for receiving signals from the microphone and the tachometer, which control circuit includes filters, analog to digital converters, signal processors, digital to analog converters, and amplifiers which generate piezoelectric element signals;

a motor shaft driven in a circular motion by a motor, which motor shaft supports at least one blade;

a piezoelectric transducer mounted to each blade; and a slip ring which receives at least one piezoelectric element signal from the control circuit and which connects at least one piezoelectric element signal to at least one piezoelectric element whereby at least one piezoelectric element is caused to vibrate in at least one frequency.

40. Apparatus of claim 39 wherein each piezoelectric element receives the same signal from the control circuit.

41. Apparatus of claim 39 wherein each piezoelectric element receives a signal which is different in phase from signals directed to other piezoelectric elements.

42. Apparatus of claim 39 wherein each piezoelectric element receives a signal which is different in phase from signals directed to other piezoelectric elements.

43. Apparatus of claim 39 wherein each piezoelectric element receives a signal which is different in frequency from signals directed to other piezoelectric elements.

44. A method for the active control of noise generated by rotating a machinery comprising:

generating an error signal;

sensing machinery motion for generating a motion signal;

processing the aforementioned signals for generating an actuator signal; and driving an actuator mounted upon the rotating machinery according to the actuator signal.

45. The method of claim 44 wherein the processing step comprises:

filtering frequency components of said signals;

converting filtered analog signals to digital form;

comparing digital signals with an algorithm;

generating an actuator signal;

converting the actuator signal from digital to analog form; and driving an actuator whereby forces are impressed upon the rotating machinery to cancel noise generated therein.

46. The method of claim 44 wherein the processing step comprises:

filtering frequency components of said signals;

comparing analog signals within analog control circuitry;

generating an actuator signal; and driving an actuator whereby forces are impressed upon the rotating machinery to cancel noise therein.

47. A method for the active control of noise generated by an air moving device comprising:

generating an error signal;

sensing machinery motion for generating a motion signal;

filtering frequency components of the motion signal and the error signal;

converting filtered analog signals to digital form;

comparing digital signals with an algorithm;

generating an actuator signal;

converting the actuator signal from digital to analog form; and driving an actuator mounted directly upon the rotating machinery.

48. A method for the active control of noise generated by rotating machinery comprising:

sensing forces caused by the rotating machinery for generating a machine force signal;

generating an error signal;

processing the aforementioned signals for generating an actuator signal;

driving an actuator mounted directly upon the rotating machinery.

49. The method of claim 48 wherein the processing step comprises:

filtering frequency components of said signals;

converting analog signals to digital form;

comparing digital signals with an algorithm;

generating an actuator signal;

converting the actuator signal from digital to analog form; and driving an actuator mounted on the rotating machinery whereby forces are impressed upon the rotating machinery to cancel tones generated therein.

50. The method of claim 48 wherein the processing step comprises:

filtering frequency components of said signals;

comparing analog signals within analog control circuitry;

generating an actuator signal; and driving an actuator whereby forces are impressed upon the rotating machinery to cancel noise therein.

51. A method for the active control of noise generated by an air moving device comprising:

sensing forces caused by the rotating machinery for generating a machine force signal;

generating an error signal;

converting the machine force signal and the error signal to digital form;

applying an algorithm to said digital signals;

generating an actuator signal;

converting the actuator signal to analog form; and driving an actuator mounted on the air moving device whereby the forces are impressed upon an impeller to control noise.

52. A method for the active control of rotating machinery noise comprising:

generating at least one error signal;

sensing machinery motion for generating a motion signal;

processing the error signal and the motion signal for generating at least one piezoelectric element signal; and directing a piezoelectric element signal to at least one piezoelectric element mounted on a blade of a motor shaft which is driven by the machinery.

53. The method of claim 52 wherein the processing step comprises:

filtering the frequency components of the error signal and the motion signal;

comparing analog signals within analog control circuitry;

generating an actuator signal; and driving an actuator whereby forces are impressed upon the rotating machinery to cancel noise therein.

54. The method of claim 52 wherein the processing step comprises:

filtering frequency components of the error signal and the motion signal;

converting filtered analog signals to digital form;

comparing digital signals with an algorithm;

generating piezoelectric element signals;

converting piezoelectric element signals from digital to analog form; and driving at least one piezoelectric element to induce vibrations therein whereby tones caused by the blades and their drive motor are reduced.

55. The method of claim 52 whereby all the piezoelectric element signals are equal in phase and amplitude.

56. The method of claim 52 wherein each piezoelectric element receives a signal which is different in phase from signals directed to other piezoelectric elements.

57. The method of claim 52 wherein each piezoelectric element receives a signal which is different in amplitude from signals directed to other piezoelectric elements.

58. The method of claim 52 wherein each piezoelectric element receives a signal which is different in frequency from signals directed to other piezoelectric elements.

59. A method for the active control of air moving device tones comprising:

generating an error signal;

sensing machinery motion for generating a motion signal;

filtering frequency components of the motion signal and the error signal;

converting filtered analog signals to digital form;

comparing digital signals with an algorithm;

generating piezoelectric element signals;

converting the piezoelectric element signals from digital to analog form; and driving at least one piezoelectric element mounted to a motor shaft driven in a circular motion by a drive motor, which motor shaft supports at least one blade.

60. The method of claim 59 whereby all the piezoelectric element signals are equal in phase and amplitude.

61. The method of claim 59 wherein each piezoelectric element receives a signal which is different in phase from signals directed to other piezoelectric elements.

62. The method of claim 59 wherein each piezoelectric element receives a signal which is different in amplitude from signals directed to other piezoelectric elements.

63. The method of claim 59 wherein each piezoelectric element receives a signal which is different in frequency from signals directed to other piezoelectric elements.

* * * * *